United States Patent
Tanimoto et al.

(10) Patent No.: US 6,951,746 B2
(45) Date of Patent: *Oct. 4, 2005

(54) METHOD OF MANUFACTURING POLYAMINE COMPOSITION

(75) Inventors: Yoshihiro Tanimoto, Kawagoe (JP); Takafumi Yakabe, Tsurugashima (JP); Taku Nakano, Sayama (JP); Masaharu Shimatani, Sayama (JP)

(73) Assignee: Snow Brand Milk Products Co., Ltd., Sapporo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,999

(22) Filed: Feb. 29, 2000

(65) Prior Publication Data

US 2002/0110880 A1 Aug. 15, 2002

(30) Foreign Application Priority Data

Mar. 4, 1999 (JP) .......................................... 11-056833

(51) Int. Cl.$^7$ ................................................. C12P 13/00

(52) U.S. Cl. .................... 435/128; 435/259; 435/254.2; 435/254.1; 435/255.1; 435/129; 424/93.51

(58) Field of Search .............................. 435/255.1, 129, 435/254.1, 259, 254.2, 128; 424/93.51

(56) References Cited

U.S. PATENT DOCUMENTS

| | | | | | |
|---|---|---|---|---|---|
| 3,961,080 A | * | 6/1976 | Sugimoto | ..................... | 426/60 |
| 4,021,303 A | * | 5/1977 | Nakabayashi | ............... | 426/656 |
| 4,303,680 A | * | 12/1981 | Tanekawa | ..................... | 426/60 |
| 4,810,509 A | * | 3/1989 | Kanegae | ...................... | 426/60 |
| 5,629,185 A | * | 5/1997 | Stanzl | ..................... | 435/173.7 |

FOREIGN PATENT DOCUMENTS

| | | | |
|---|---|---|---|
| JP | 54017167 | * | 7/1977 |
| JP | 09117263 | * | 5/1997 |
| JP | 10052291 | * | 2/1998 |
| JP | 10 262607 | | 10/1998 |
| WO | WO 98/52552 A | | 11/1998 |

* cited by examiner

Primary Examiner—Irene Marx
(74) Attorney, Agent, or Firm—Knobbe, Martens, Olson & Bear LLP

(57) ABSTRACT

After yeast somatic components are digested with nuclease or hydrolyzed with alkali, polyamine is recovered to obtain a polyamine composition in volume efficiently at a high recovery rate from yeast somatic components.

10 Claims, No Drawings

METHOD OF MANUFACTURING POLYAMINE COMPOSITION

BACKGROUND OF THE INVENTION

1. Field of the Invention

This invention relates to a method of manufacturing a polyamine composition from yeast somatic components efficiently and in volume. In detail, it relates to a method of manufacturing a polyamine composition, wherein after digesting yeast somatic components with nuclease or hydrolyzing them with alkali, polyamine is recovered. When manufacturing a polyamine composition from yeast somatic components, by applying the method of this invention, the recovery of polyamine can be improved.

2. Description of the Related Art

A polyamine is a general term for straight chain aliphatic hydrocarbon containing more than two primary amino groups, and as typical polyamines, putrescine, spermidine and spermine can be mentioned. As polyamines' physiological functions, (1) cell proliferation action, (2) cell differentiation accelerating action, (3) an immune essential factor, (4) antiallergic action, (5) protein synthesis acceleration action, (6) structural stabilization by interaction with nucleic acid, (7) enzyme activation regulating action, etc. are known. Recently, many reports have been made that orally taken polyamine accelerates proliferation and differentiation of mucosal cells of the alimentary canal (O. Peulen et al., Arch. Physiol. Biochem., vol.106, pp. 46–55, 1998; W. P. Deloyer et al., Arch. Physiol., Biochem., vol.104, pp. 163–172, 1996; M. Kaouass et al., Dig., Dis. Sci., vol. 41, pp.1434–1444, 1996; E. Harada et al., Comp. Biochem. Physiol., vol.109A, pp.667–673, 1994; G. Capano et al., J. Pediatr. Gastroenterol. Nutr. vol.19, pp.34–42, 1994; G. E. Wild et al., Biol. Neonate, vol.63, pp.246–257, 1993; Buts J. -P. et al., Digestive Diseases and Science, vol.38, p.1091, 1993; Dufour, C. et al., Gastroenterology, vol.95, p.112, 1988).

According to these reports, physiological effects of spermidine and spermine were examined and it was also made clear that spermine has a stronger action than does spermidine to accelerate the alimentary canal to mature. Further, it was reported that orally taken polyamine is quickly absorbed into the body and taken up and utilized by tissues. It was also reported that spermidine and spermine are absorbed more quickly than putrecine (Bardocz, S. et al., J. Nutr. Biochem., vol.4, p.66, 1993).

As examples of using polyamine for food, konnyaku (a jelly-like food made from the starch of devil's tongue) to which spermidine and spermine are added to reduce a smell peculiar to konnyaku and which does not have a bad effect if it is cooked with other foods (Japanese Patent Laid-open No.1994-38690) and a polyamine-mixed nutritional composition to which polyamine is mixed to accelerate protein absorption for the purpose of maintaining satisfactory growth and health conditions (Japanese Patent Laid-open No.1994-305956) and others have been proposed. In addition, as examples of using polyamine as medicines, a method of stopping gastric acid secretion and a composition for intake for the purpose of stopping gastric acid secretion (Japanese Patent Laid-open No.1983-131914) and immune activator (Japanese Patent Laid-open No.1984-98015 and Japanese Patent Laid-open No.1990-223514) and others have been Proposed.

Incidentally, it is known that meats and fermented foods such as cheese and miso (soybean paste) contain more polyamine than do milk and vegetables (Bardocz, S. et al., J. Nutr. Biochem., vol.4, p.66, 1993; Polyamine Society 12th Meeting for Reading Research Papers Lectures Outline, p.4, 1995). Consequently, the amount of polyamine contained in nutritional compositions of infant formula and others, of which milk is the main ingredient, is very small. Additionally, it was reported that human milk contained a relatively large amount of polyamine (Japanese Journal of Pediatric Gastroenterology and Nutrition, vol.1.9, no.2, pp.115–121, 1995) and it can be said that it is preferable from a physiological point of view to enrich polyamine in nutritional compositions with a low polyamine content.

Further, as a nutritional composition with high polyamine content, proteolytic milk has been introduced by Buts and others (Buts, J. P. et al., J. Pediatr. Gastroenterol. Nutr., vol.21, p.44, 1995), but polyamine contained in this proteolytic milk is polyamine derived from natural enzymes used for proteolysis and it is not intended as enrichment of polyamine.

Moreover, a method of manufacturing polyamine from yeast and a nutritional composition to which polyamine manufactured by this method is mixed have been proposed (Japanese Patent Laid-open No.1998-52291). In this method, polyamine without an offensive smell and taste can be manufactured by treating yeast under acidic conditions. However, under acidic conditions, because a part of polyamine precipitates together with a high molecular-weight substance, all the polyamine contained in yeast could not be recovered. Additionally, a part of polyamine is bound in vivo with a high molecular-weight substance, not all polyamine could be recovered simply by performing fractionation.

SUMMARY OF THE INVENTION

The inventors of this invention have earnestly worked on research to develop a method of manufacturing a polyamine composition in volume, and discovered that a polyamine composition could be recovered at an efficient recovery rate by digesting yeast somatic components with nuclease or hydrolyzing them with alkali. This discovery led to developing this invention. Consequently, a problem that this invention intends to solve is to provide a method of manufacturing a polyamine composition from yeast somatic components at an efficient recovery rate.

In this invention, when manufacturing a polyamine composition, yeast somatic components are used as a raw material, and after digesting these yeast somatic components with nuclease or hydrolyzing them with alkali, polyamine is recovered.

Yeast somatic components that can be used as a raw material in this invention can be prepared from bread yeast, wine yeast, beer yeast, torula yeast and others, by physically crushing, by using hot water, or by autolysis.

As a method of extracting the yeast somatic components by physically crushing yeast, for example, the yeast can be crushed using a high-pressure homogenizer and an ultrasonic disintegrator and the yeast somatic components can be extracted.

Furthermore, it is preferable to use a high-pressure homogenizer that can damage cell walls and cell membranes, that can cause exchange of somatic liquid and extracellular liquid, and that has a pressure capacity of more than 700 kgf/cm$^2$. Using such a high-pressure homogenizer, yeast can be crushed by using pressure of 700~1, 400 kgf/cm$^2$. This type of high-pressure homogenizer is manufactured by Rannie, Gaulin, Nihon Seiki and other companies. Moreover, it is preferable to use an ultrasonic disintegrator that can destroy cells mechanically. Using such an ultrasonic disintegrator, yeast suspension can be crushed at 10~90 kHz from several tens seconds to several minutes divided into several times. This type of ultrasonic disintegrator is manufactured by Branson, Ultrasonic, Rayton and other companies.

As a method of extracting yeast somatic components from yeast using hot water, for example, common salt is added to a yeast suspension with a yeast concentration of 5~25%, preferably 10~20%, to make a salt concentration of 1~10%, preferably 4~8%, and the yeast somatic components are extracted by warming it at a pH value of 4~8, preferably a pH value of 5~7, and at a temperature of 90~100° C. (194~212° F.), preferably 95~100° C. (203~212° F.), for one to five hours, preferably three to five hours.

As a method of extracting yeast somatic components by autolyzing yeast, for example, autolysis of the yeast can be accelerated by adding an autolysis accelerator such as salt, fatty acid ester, organic acid, organic solvent, etc. which can be used when manufacturing yeast extract (Japanese Patent Publication No.1979-13496, Japanese Patent Laid-open No.1980-34096, Japanese Patent Laid-open No.1984-109152). Moreover, autolysis of the yeast can be accelerated by using mechanical stimuli by ultrahigh-pressure static hydraulic pressure processing, ultrasonication, high-pressure homogenizer processing and others (Japanese Patent Laid-open No.1990-255059, Japanese Patent Publication No.1975-25539).

Further, by maintaining the yeast at a temperature of 37~55° C. (98.6~131° F.), protein and RNA within the yeast are autolyzed and hydrolyzed to amino acid or 3'-nucleoside, 5'-nucleoside respectively.

Moreover, yeast extracts and yeast RNA on the market can also be used as yeast somatic components. As yeast extracts on the market, for example, RN, RN7, RT, RN7-P, RB2-P, RT-P (the mentioned above are manufactured by Sapporo Agency); Meast S, Meast N, Meast PIG, Super-Meast R-1, SuperMeast Powder A-001, SuperMeast R-7, Dry Beer Yeast Y2A, Beer Yeast Extract (Ebios) P2G (the mentioned above are manufactured by Asahi Beer Food); Dry Beer Yeast (the mentioned above are manufactured by Asahi Beer Pharmaceutical); Yeast Extract C, Yeast Extract W, Yeast Extract L, Yeast Extract H (the mentioned above are manufactured by Kyowa Hakko Kogyo); Yeast Extract Emic YG (the mentioned above are manufactured by Tanabe Pharmaceutical); Dry Beer Yeast BY-S, Debittered Yeast BY-G and Yeast RNA (the mentioned above are manufactured by Kirin Brewery) can be used.

In this invention, as a method of digesting yeast somatic components with nuclease, for example, nuclease is added to a solution containing the yeast somatic components and this solution is treated at a pH value of 3~10 and at a temperature of 10~70° C. (50~158° F.) for 0.1~24 hours. As nuclease used, any nucleases such as deoxyribonuclease I, nuclease, nuclease P1, nuclease S1, phosphodiesterase I, ribonuclease A, ribonuclease B, ribonuclease $T_1$, ribonuclease $T_2$, ribonuclease $U_2$ and others, which has a characteristic of hydrolyzing nucleic acid, can be used. The yeast somatic components can be treated using nuclease on the market as is, or can be treated using tissues of a plant or an animal, microbial body, microbial culture media and others, which exhibit nuclease activity. Furthermore, it is possible to use nuclease, which is contained in the yeast somatic components to be used, for the treatment.

In this invention, as a method of hydrolyzing yeast somatic components with alkali, for example, alkali is added to a solution containing the yeast somatic components to make it 0.1~5N and this solution is treated at 20~100° C. (68~212° F.) for 0.1~24 hours. As alkali used, sodium hydrate and potassium hydroxide can be mentioned.

In this way, after digesting yeast somatic components with nuclease or hydrolyzing them with alkali, by recovering polyamine, a polyamine composition can be manufactured.

DETAILED DESCRIPTION OF THE PREFERRED EMBODIMENT

The present invention can be conducted in various ways as explained below.

Using yeast somatic components prepared from bread yeast, beer yeast, torula yeast and others or with yeast extracts or yeast RNA on the market used as yeast somatic components, these yeast somatic components are digested with nuclease or hydrolyzed with alkali. By recovering polyamine, a polyamine composition can be manufactured. The polyamine composition obtained in this method can be used as is as a solution, or it can be used as a powder after spray-drying, freeze-drying, etc. Furthermore, after desalting or purification, it can be used as is as a solution or as a powder.

Incidentally, if yeast extracts or yeast RNA on the market are used as yeast somatic components, by treating the yeast extracts or yeast RNA using acid once or several times beforehand, discarding a supernatant, recovering a precipitate and using this precipitate as the yeast somatic components, the content ratio of spermidine and spermine, which are polyamines with a high physiological effect, can be increased and the ratio of these polyamines can be controlled as well.

Moreover, after digesting yeast somatic components with nuclease or hydrolyzing them with alkali, by deproteinizing them, polyamine content can be increased, and further, a purification load can be reduced. As a method for deproteinization from a polyamine solution, acid treatment, salting out, proteinase digestion and others can be used.

As a method for deproteinization using acid treatment, for example, after cooling down a polyamine solution to lower than 10° C. (50° F.), acid is added to it to bring the pH value to less than two, the solution is left as is for two to six hours, a precipitate generated is removed and a supernatant is recovered. As acid used, inorganic acids and organic acids including sulfuric acid, hydrochloric acid, acetic acid, phosphoric acid, trichloroacetic acid, perchloric acid, sulfosalicylic acid, formic acid and other can be used.

As a method for deproteinization using salting out, for example, a salt such as iron chloride is added to a polyamine solution and the solution is heated. Protein and other impurities are flocculated by centrifugal separation or other treatments and removed and a supernatant is recovered. Alternatively, a salt such as ammonium sulfate is added to a polyamine solution, the solution is cooled to lower than 5° C. (41° F.), and protein is flocculated by centrifugal separation or other treatments and removed, and a supernatant is recovered.

As a method of deproteinization using proteinase digestion, for example, a protease is added to a polyamine solution and the solution is treated at a pH value of 1~10 and at a temperature of 10~70° C. (50~158° F.) for 0.1~24 hours. As proteases used, any proteases that have a characteristic of deproteinization including proteases derived from animals and plants such as trypsin and papain or proteases to which microbes such as aspergillus group fungi, rhizopus group fungi and bacillus group fungi grow, and a protease on the market can also be used as is for the treatment. Tissues of plants and animals which have protease activity, microbial body, and microbial culture media can also be used for the treatment.

As the need arises, using a means such as ion-exchange resin treatment, membrane fractionation and electrodialysis, the polyamine solution can be desalted or purified. Further, by combining these means properly, a polyamine composition with higher purity can be obtained.

As a method for the ion-exchange resin treatment, for example, a polyamine solution is passed through a column filled with ion-exchange resin and polyamine is separated from unwanted components such as amino acids, peptides, protein and sugars. For ion-exchange resin, the only requirement is that its ion-exchange group should be a sulfonic group, a sulfopropyl group, a phosphoric acid group, a carboxlmethyl group, an aminoethyl group, a diethylamino group, a quaternary aminoethyl base or a quaternary ammonium base, and either cation-exchanbe resin or anion-exchange resin can be used. Furthermore, if cation-exchanbe resin is used, because polyamine is adsorbed to the cation-exchanbe resin, after non-adsorped components are sufficiently separated, polyamine is recovered by eluting it using an acidic solvent such as sulfuric acid and hydrochloric acid or a saline such as sodium chloride. If anion-exchange resin is used, because polyamine is not adsorbed to the anion-exchange resin, a non-adsorped fraction that contains polyamine can be recovered.

As a method for membrane fractionation, for example, using an ultrafilter membrane (UF) of cellulose, cellulose acetate, polysulfone, polyamide, polyacrylonitrile, poly(4-ethlene fluoride), polyester, polypropylene and others with the fractionation molecule weight within the range of 1,000~100,000, UF of a polyamine solution is conducted and transmitted liquid containing polyamine is recovered. Another method that can be used for desalting is to perform nanofiltration (NF) of the polyamine solution using an NF membrane with a salt blocking coefficient of 30~80%.

As a method for electrodialysis, for example, the electrodialysis can be done by supplying a polyamine solution and brine alternately through each of a cation-exchange membrane and an anion-exchange membrane.

Further, as conditions for the electrodialysis, initial current density of 0.5~15A/dm$^2$ and voltage of 0.1~1.5V/tank are preferable.

Polyamine compositions obtained in this way can be used for nutritional compositions for medical use, nutritional compositions for infant products such as infant formula and baby food and further an additive for nutritionally enriched food and general foods.

Next, examples and comparative examples are shown to explain this invention in more detail. Analyses of the polyamine content in the examples and the comparative examples were performed according to the method by Kawakami and others (Japanese Journal of Pediatric Gastroenterology and Nutrition, vol.1.9, pp.115–121, 1995).

EXAMPLE 1

Using torula yeast (*Candida utilis*), a polyamine composition was manufactured by digesting yeast somatic components with nuclease.

Torula yeast (*Candida utilis*) was planted in a molasses culture medium and aeration spinner culture was conducted at 30° C. (86° F.) for 48 hours. After culturing the yeast, the medium was centrifuged (5,000 g) at 4° C. (39.2° F.) for 30 minutes and yeast was gathered. After rinsing the yeast gathered with cold water, a yeast suspension with a yeast concentration of 15% was prepared, and yeast somatic components were extracted under the conditions of: a salt concentration of 4.8%, a pH value of 6.0, a temperature of 95° C. (203° F.) for three and half hours.

Iron chloride was added to this yeast somatic components solution, and after adjusting the pH value to 5.0, the solution was heated at 90° C. (194° F.) for 90 minutes to condense protein and other unwanted components. After filtrating the solution through diatomaceous earth and recovering a supernatant, this supernatant was cooled to 5° C. (41° F.), the pH value was adjusted to 1.5 by adding hydrochloric acid and the supernatant was left undisturbed for approximately four hours and polyamine was precipitated and recovered. After suspending this precipitate in water by adding 30% sodium hydrate, the pH value was adjusted to 6.0 and the precipitate was dissolved by adding 1 mg/ml of ribonuclease A (manufacture by Kanto Kagaku), it was digested at 25° C. (77° F.) for 15 hours and a polyamine solution was obtained.

After this polyamine solution was passed through a column filled with cation-exchange resin (Dowex 50WX8 [H$^+$ type]) and polyamine was adsorbed to the cation-exchange resin, 0.7M brine was passed through the column, the resin was rinsed sufficiently and impurities were removed, and then the polyamine adsorbed was eluted using 6N hydrochloric acid. By adding a 30% sodium hydrate solution to this eluate to neutralize it, it was desalted by electrodialysis and freeze-dried and a polyamine composition was obtained.

In this way, 698 mg of polyamine composition containing 465 mg of polyamine per 1 kg of yeast (wet weight) was obtained. This yield was three times more than the yield of polyamine composition obtained by a conventional method (Comparative example 1). Of 465 mg of polyamine, the total amount of spermidine and spermine was 446 mg and the percentage of spermidine and spermine in the whole polyamine was increased to 96%.

EXAMPLE 2

Using wine yeast (*Saccharomyces cerevisiae*), a polyamine composition was manufactured by digesting yeast somatic components with nuclease.

Wine yeast (*Saccharomyces cerevisiae*) was suspended in water and a 10% yeast suspension was prepared and was physically crushed using a high-pressure homoginizer (manufactured by Rannie, Type 10.51VH) at a pressure of 1,000 kgf/cm$^2$, and yeast somatic components were extracted. 30% sodium hydrate was added to these yeast somatic components solution and the pH value was adjusted to 8.0. 1 mg/ml each of ribonuclease A (manufactured by Kanto Kagaku), trypsin (manufactured by Berlingermanheim [BMKK]) was added, the solution was digested at 37° C. (98.6° F.) for 18 hours and a polyamine solution was obtained.

After high molecular-weight substances such as remaining enzymes and undecomposed protein were removed by performing the UF to this polyamine solution using a PLCC cellulose membrane (with the fractionated molecular weight of 5,000, manufactured by Millipore), by passing the UF permeate through a column filled an anion-exchange resin (Dowex 1X8 [Cl$^-$ type]), unwanted amino acids were removed by adsorbing them to the anion-exchange resin and a non-adsorbed fraction was recovered. This solution was then freeze-dried and a polyamine composition was obtained.

In this way, 183 mg of polyamine composition containing 87 mg of polyamine per 1 kg (wet weight) of yeast was obtained. This yield was 2.1 times more than the yield of polyamine composition obtained by a conventional method (Comparative example 2). Of 87 mg of polyamine, the total amount of spermidine and spermine was 82.7 mg and the percentage of spermidine and spermine in the whole polyamine was increased to 95%.

EXAMPLE 3

Using yeast RNA (manufactured by Kirin Brewery) as yeast somatic components, a polyamine composition was manufactured by hydrolyzing the yeast somatic components with alkali.

A polyamine composition was dissolved in 0.3N sodium hydrate to obtain a 5% yeast RNA and was hydrolyzed at 37° C. (98.6° F.) for 18 hours and a polyamine solution was obtained.

After this polyamine solution was passed through a column filled with cation-exchange resin (Dowex 50WX8 [H+ type]) and polyamine was adsorbed to the cation-exchange resin, 0.5M brine was passed through the column, the resin was rinsed sufficiently and impurities were removed, and then adsorbed polyamine was eluted using 6N hydrochloric acid. After neutralizing this eluate by adding a sodium hydrate solution, it was desalted by electrodialysis and freeze-dried and a polyamine composition was obtained.

In this way, 1,750 mg of polyamine composition containing 1,460 mg of polyamine per 1 kg of yeast RNA was obtained. This yield was 3.2 times more than the yield of polyamine composition obtained by a conventional method (Comparative example 3). Of 1,460 mg of polyamine, the total amount of spermidine and spermine was 1,431 mg and the percentage of spermidine and spermine in the whole polyamine was increased to 98%.

EXAMPLE 4

Using bread yeast (*Saccharomyces cerevisiae*), a polyamine composition was manufactured by autolyzing yeast somatic components.

After bread yeast (*Saccharomyces cerevisiae*) was suspended in water and 20% yeast suspension was prepared, 1 Kg of this yeast suspension was transferred to a 2-liter flask and by adding 8 g of lactic acid, it was autolyzed at 45° C. (113° F.) for 24 hours. Autolysis was then stopped by heating the suspension to 90° C. (194° F.) and maintaining this temperature for 10 minutes, and a polyamine solution was obtained.

After this polyamine solution was passed through a column filled with a cation-exchange resin (Dowex 50WX8 [H+ type]) and polyamine was adsorbed to the cation-exchange resin, 0.6M brine was passed through the column, the resin was rinsed sufficiently and impurities were removed, and adsorbed polyamine was then eluted using 6N hydrochloric acid. After neutralizing this eluate by adding sodium hydrate, it was desalted by electrodialysis and spray-dried and polyamine was obtained. This solution was then spray-dried and a polyamine composition was obtained.

In this way, 314 mg of polyamine composition containing 95 mg of polyamine per 1 kg (wet weight) of yeast was obtained. Of 95 mg of polyamine, the total amount of spermidine and spermine was 88.4 mg.

Comparative EXAMPLE 1

Using torula yeast (*Candida utilis*), a polyamine composition was manufactured.

Torula yeast (*Candida utilis*) was planted in a molasses culture medium and aeration spinner culture was conducted at 30° C. (86° F.) for 48 hours. After culturing the yeast, the medium was centrifuged (5,000 g) at 4° C. (39.2° F.) for 30 minutes and yeast was collected. After rinsing the collected yeast with cold water, a yeast suspension with a yeast concentration of 15% was prepared, and yeast somatic components were extracted under the conditions of: a salt concentration of 4.8%, a pH value of 6.0, a temperature of 95° C. (203° F.) for 3.5 hours.

Iron chloride was added to this yeast somatic components solution, and after adjusting the pH value to 5.0, the solution was heated at 90° C. (194° F.) for 90 minutes to condense protein and other unwanted components. After suction filtrating the solution using Celite (manufactured by John Manbill) and recovering a supernatant, this supernatant was cooled to 5° C. (41° F.), the pH value was adjusted to 1.5 by adding hydrochloric acid and the supernatant was left undisturbed for four hours and polyamine was precipitated and recovered. After suspending this precipitate in water, by adding 30% sodium hydrate, the pH value was adjusted to 6.0, the precipitate was dissolved, and a polyamine solution was obtained.

After this polyamine solution was passed through a column filled with cation-exchange resin (Dowex 50WX8 [H+ type]) and polyamine was adsorbed to the cation-exchange resin, 0.7M brine was passed through the column, the resin was rinsed sufficiently and impurities were removed, and adsorbed polyamine was then eluted using 6N hydrochloric acid. After adding a 30% sodium hydrate solution to this eluate to neutralize it, it was desalted by electrodialysis and freeze-dried and a polyamine composition was obtained.

In this way, 500 mg of polyamine composition containing 155 mg of polyamine per 1 kg (wet weight) of yeast was obtained. Of 155 mg of polyamine, the total amount of spermidine and spermine was 142.6 mg (92%).

COMPARATIVE EXAMPLE 2

Using wine yeast (*Saccharomyces cerevisiae*), a polyamine composition was manufactured.

Wine yeast (*Saccharomyces cerevisiae*) was suspended in water and 10% yeast suspension was prepared and was physically crushed using a high-pressure homoginizer (manufactured by Rannie, Type 10.51VH) at a pressure of 1,000 kgf/cm², and yeast somatic components were extracted.

After high molecular-weight substances were removed by performing UF on this yeast somatic components solution using a PLCC cellulose membrane (with the fractionated molecular weight of 5,000, manufactured by Millipore), by passing the UF-permeate through a column filled with anion-exchange resin (Dowex 1X8 [Cl- type]), unwanted amino acids were removed by adsorption to the anion-exchange resin and a non-adsorbed fraction was recovered. This solution was then freeze-dried and a polyamine composition was obtained.

In this way, 220 mg of polyamine composition containing 42 mg of polyamine per 1 kg (wet weight) of yeast was obtained. Of 42 mg of polyamine, the total amount of spermidine and spermine was 37.8 mg (90%).

COMPARATIVE EXAMPLE 3

Using yeast RNA (manufactured by Kirin Brewery) as yeast somatic components, a polyamine composition was manufactured.

A polyamine composition was dissolved in water to obtain a 5% yeast RNA and a polyamine solution was obtained.

After this polyamine solution was passed through a column filled with cation-exchange resin (Dowex 50WX8 [H$^+$ type]) and polyamine was adsorbed to the cation-exchange resin, 0.5M brine was passed through the column, the resin was rinsed sufficiently and impurities were removed, and adsorbed polyamine was then eluted using 6N hydrochloric acid. After neutralizing this eluate by adding a sodium hydrate solution, it was desalted by electrodialysis and freeze-dried and a polyamine composition was obtained.

In this way, 550 mg of polyamine composition containing 460 mg of polyamine per 1 kg of yeast RNA was obtained. Of 460 mg of polyamine, the total amount of spermidine and spermine was 437 mg (95%).

Efficacy of the Invention

When manufacturing in volume a polyamine composition from yeast somatic components, by applying the method of this invention, the recovery of polyamine can be increased. In addition, of the polyamine, the percentage of spermidine and spermine, which are known to be effective, can also be increased.

What is claimed is:

1. A method of obtaining polyamines, comprising the steps of:

providing a yeast RNA-containing composition;

subjecting said yeast RNA-containing composition to a decomposition step, comprising nuclease digestion or alkali hydrolysis, for increasing the yield of polyamines recovered in a subsequent recovery step by approximately 2–3.2 times the yield of polyamines recovered in the subsequent recovery step without this decomposition step, under conditions where the yield with this decomposition step when continuing for approximately 15–19 hours is approximately 2–3.2 times the yield without this decomposition step, wherein said yeast RNA-containing composition is treated in solution with nuclease added in an effective concentration, at approximately 25–37° C., and at a pH of approximately 6–8, or said yeast RNA-containing composition is dissolved in a 0.3 N alkali solution at 37° C.; and recovering the approximately 2–3.2 times greater yield of polyamines from the decomposed yeast RNA-containing composition produced.

2. The method according to claim 1, wherein said nuclease is a nuclease contained in the yeast RNA-containing composition.

3. The method according to claim 1, wherein the yeast RNA-containing composition is obtained from yeast selected from the group consisting of *Saccharomyces cerevisiae* and *Candida utilis*.

4. The method according to claim 1, wherein the yeast RNA-containing composition is an extract obtained by physically crushing yeast using a high-pressure homogenizer and an ultrasonic disintegrator.

5. The method according to claim 1, wherein the yeast RNA-containing composition is an extract obtained from yeast using hot water at a pH value of 4–8 and at a temperature of 90–100° C., wherein sodium chloride is added to a yeast suspension with a yeast concentration of 5–25% to make a salt concentration of 1–10%.

6. The method according to claim 1, wherein the yeast RNA-containing composition is an extract obtained by autolyzing yeast.

7. The method according to claim 1, wherein the nuclease is selected from the group consisting of nuclease P1, nuclease S1, phosphodiesterase I, ribonuclease A, ribonuclease B, ribonuclease $T_1$, ribonuclease $T_2$, and ribonuclease $U_2$.

8. The method according to claim 1, wherein the alkali is sodium hydroxide or potassium hydroxide.

9. A method of obtaining polyamines, comprising:

a step for providing a yeast RNA-containing composition;

a step for subjecting said yeast RNA-containing composition to a decomposition step, comprising nuclease digestion or alkali hydrolysis, for increasing the yield of polyamines recovered in a subsequent recovery step by approximately 2–3.2 times the yield of polyamines recovered in the subsequent recovery step without this decomposition step, under conditions where said yeast RNA-containing composition is treated in solution with nuclease added in an effective concentration, at approximately 25–37° C., and at a pH of approximately 6–8, or said yeast RNA-containing composition is dissolved in a 0.3 N alkali solution at 37° C.; and a step for recovering the approximately 2–3.2 times greater yield of polyamines from the decomposed yeast RNA-containing composition produced.

10. The method according to claim 9, wherein the decomposition step is conducted hydrolyzing at 20–100° C. the yeast RNA-containing composition with sodium hydroxide.

* * * * *

UNITED STATES PATENT AND TRADEMARK OFFICE
CERTIFICATE OF CORRECTION

PATENT NO.         : 6,951,746 B2
APPLICATION NO. : 09/514999
DATED                  : October 4, 2005
INVENTOR(S)        : Yoshihiro Tanimoto et al.

It is certified that error appears in the above-identified patent and that said Letters Patent is hereby corrected as shown below:

Column 1, Line 65, please delete "Proposed." and insert -- proposed. --, therefor.
Column 5, Line 19 (Approx.), please delete "exchanbe" and insert -- exchange --, therefor.
Column 5, Line 20 (Approx.), please delete "exchanbe" and insert -- exchange --, therefor.
Column 5, Line 22 (Approx.), please delete "exchanbe" and insert -- exchange --, therefor.
Column 6, Line 12, please delete "supematant," and insert -- supernatant, --, therefor.
Column 6, Line 14, please delete "supematant" and insert -- supernatant --, therefor.
Column 6, Line 48-54, please delete "30% sodium hydrate was....solution was obtained." and insert the same at line 49 as a new paragraph.
Column 9, Line 34, In Claim 1, please delete "15-19" and insert -- 15-18 --, therefor.
Column 10, Line 43, In Claim 10, after "conducted" please insert -- by --.

Signed and Sealed this

Twelfth Day of December, 2006

JON W. DUDAS
*Director of the United States Patent and Trademark Office*